United States Patent [19]

Manko

[11] Patent Number: 5,579,916

[45] Date of Patent: Dec. 3, 1996

[54] FEMININE HYGIENE CARRIER KIT

[76] Inventor: Katrina A. Manko, 505-A Cherry Tree Rd., Aston, Pa. 19014-1503

[21] Appl. No.: 375,717

[22] Filed: Jan. 20, 1995

[51] Int. Cl.$^6$ .......................... B65D 69/00; A45D 40/00; A45D 42/14
[52] U.S. Cl. .......................... 206/581; 132/312; 150/118; 206/440; 206/494; 248/206.2
[58] Field of Search .................... 132/286, 312; 206/233, 438, 440, 494, 581, 812, 205, 829, 806; 150/118, 131; 248/205.5, 206.2, 683, 301, 303, 304, 206.3

[56] References Cited

U.S. PATENT DOCUMENTS

| | | | |
|---|---|---|---|
| 398,679 | 2/1889 | White | 248/205.5 |
| 1,722,507 | 7/1929 | Stanley . | |
| 1,915,007 | 6/1933 | Weiss | 206/581 |
| 1,919,012 | 7/1933 | Diskin | 132/312 |
| 2,062,237 | 11/1936 | Schwartz | 206/581 |
| 2,068,547 | 1/1937 | Jung | 206/581 |
| 2,143,062 | 1/1939 | Ericson et al. | 206/581 X |
| 2,167,926 | 8/1939 | Glasker | 206/581 |
| 2,218,666 | 10/1940 | Tamoschat . | |
| 2,261,157 | 11/1941 | Holbrook | 206/581 |
| 2,623,566 | 12/1952 | Kibler | 206/581 X |
| 2,648,366 | 8/1953 | Higbee et al. | 206/370 X |
| 2,717,620 | 9/1955 | Renz . | |
| 2,750,033 | 6/1956 | Pickens | 206/440 X |
| 2,764,201 | 9/1956 | Whippo | 206/581 X |
| 2,804,969 | 9/1957 | Barnett . | |
| 2,876,980 | 3/1959 | Salter | 248/206.3 |
| 3,035,578 | 5/1962 | Elmore | 206/440 X |
| 3,397,706 | 8/1968 | Hogan | 132/312 |
| 3,892,369 | 7/1975 | Fujawa . | |
| 3,973,567 | 8/1976 | Srinivasan et al. | 229/87.01 X |
| 4,349,104 | 9/1982 | Hayes | 206/205 |
| 5,020,673 | 6/1991 | Adams . | |
| 5,025,928 | 6/1991 | Orosy et al. | 206/581 |
| 5,046,620 | 9/1991 | Barabino . | |
| 5,249,674 | 10/1993 | Lepie . | |
| 5,259,503 | 11/1993 | Steingraber | 206/440 |
| 5,261,531 | 11/1993 | Nieves . | |
| 5,329,947 | 7/1994 | Shikler | 206/581 X |

Primary Examiner—Bryon P. Gehman
Attorney, Agent, or Firm—Richard C. Litman

[57] ABSTRACT

A kit for carrying feminine hygiene materials, such as individually sealed sanitary napkins. The kit includes a carrying case, napkins or like wiping or absorbent products, and scented disposal bags. The case has two mutually hinged sections, which mate in clamshell fashion. The interior surfaces of the sections have elastic straps attached thereto for retaining the hygiene materials in place. The case has an external, tethered loop and a separate suction cup provided with a hook, so that the case can be suspended from a smooth environmental surface. A pocket is optionally provided integral with the case, either internally or externally, for storing the bags and the suction cup. Optionally, the bags are contained within a separate storage box. The case is bound in a washable material, such as canvas or vinyl, and is closed by a zipper. The case is small and unobtrusive, enables the hygiene kit to be carried in public with minimal embarrassment to the user, and protects the contained hygiene products from damage.

7 Claims, 7 Drawing Sheets

FEMININE HYGIENE CARRIER KIT

BACKGROUND OF THE INVENTION

1. FIELD OF THE INVENTION

The present invention relates to a kit comprising feminine hygiene products and a carrying case for the same.

2. DESCRIPTION OF THE PRIOR ART

A variety of hygiene articles for coping with the onset of menses has been made available to the public. Women must frequently carry these articles while engaging in the day's activities. Proper storage and concealment of these articles is an ongoing problem, given the range of options available to women. These options generally include stowage in a purse, or carrying the articles separately, as in a bag.

Neither option is truly satisfactory. The separate bag is unwieldy at best, and may be prone to inadvertent opening, and discharging of contents. Carrying the articles in a purse may cause damage to the articles, and furthermore risks exposure of these articles to onlookers when a woman removes an unrelated article from the purse. These articles are a source of embarrassment to many people, and consequently, it is desirable to conceal the articles.

Additionally, a woman may be obliged to select a particular hygiene article from a variety thereof. As the article will most likely become soiled and require disposal, additional articles for enabling disposal is also desirable.

A need has been recognized for developing a suitable kit comprising a satisfactory carrier and appropriate hygiene materials.

U.S. Pat. No. 5,046,620, issued to William A. Barabino on Sep. 10, 1991, recognizes the problem, and sets forth a kit having a carrying case designed to be both presentable and unobtrusive. The case differs from that of the present invention.

Personal carrying cases having internal straps for retaining articles within the case are shown in U.S. Pat. Nos. 1,722,507, issued to Leopold G. Stanley on Jul. 30, 1929, and 2,804,969, issued to Harry E. Barnett on Sep. 3, 1957. The internal retaining straps are not resilient.

U.S. Pat. Nos. 5,261,531, issued to Felipe A. Nieves on Nov. 16, 1993, and 5,249,674, issued to Eric J. Lepie on Oct. 5, 1993, disclose portable hygiene kits. In both examples, both the case and contents of the kit differ from those of the present invention.

The kits listed above are both highly specific in their contents, or may be prone to depart from the original purpose. The kit of Nieves contains certain specified items which may not satisfy the needs of a particular situation. Also, the kit contents are revealed for all to see. The kit of Barabino includes general purpose items, and thus fails to segregate hygiene articles from objects having other purposes and which are frequently retrieved for use.

A carrying case for personal items is described in U.S. Pat. No. 5,020,673 issued to David R. Adams on Jun. 4, 1991. The items are secured in pockets, rather in the manner of the present invention.

Personal carrying cases are also shown in U.S. Pat. Nos. 2,218,666, issued to William Tamoschat on Oct. 22, 1940, and 2,717,620, issued to Emil K. Renz on Sep. 13, 1955. No retaining straps are disclosed.

A suction cup device is shown in U.S. Pat. No. 3,892,369, issued to Eugene Fujawa on Jul. 1, 1975. This device is representative of devices which could be employed for the purposes of the present invention, although with modification as well as in combination with a case.

None of the above inventions and patents, taken either singly or in combination, is seen to describe the instant invention as claimed.

SUMMARY OF THE INVENTION

The feminine hygiene kit of the present invention seeks to meet the recognized needs set forth above, and needs not recognized, in a manner which is acceptable to women traveling in public. A carrying case provided to house hygiene articles and dedicated solely to this purpose is small, flat, and unobtrusive, yet of presentable appearance. The structure provided to retain hygiene articles within the case is advantageously configured for this purpose. The structure comprises straps which are elastic, so that they draw their subject articles tightly against the case, and stretch to accommodate articles of different dimensions.

The invention can be supported at a convenient point when the user employs public sanitary facilities. In such facilities, no convenient table or similar generally suitable horizontal supporting surface may be present. The case has apparatus for attachment to any smooth, rigid environmental surface, such as metal, porcelain, or synthetic resin. These materials are typically employed in counter tops and walls, plumbing fixtures, and stalls for showers or toilets.

The apparatus includes a loop tethered to the case to enable suspending the case from a hook. The kit includes a suction cup having a hook so that the case can be suspended from, especially, a vertical surface.

The articles carried within the kit include absorbent, flexible sheets or pads for stanching the flow of bodily fluids. These articles are available to the public as tampons, feminine napkins, shields, and liners. Such products are generally individually wrapped and sealed to promote sanitary conditions of use.

Disposal of these articles after use is another problem not generally recognized in the prior art. To facilitate sanitary disposal, and to overcome objectionable odors, the kit includes scented water impermeable bags. Preferably, the bags are biodegradable and opaque. Leakage and odors are contained, with the scenting presenting an additional protection against odors. A soiled article and any debris remaining from hygiene articles may therefore be deposited in any general purpose waste receptacle without objection.

A pocket is provided in the case to store the disposal bags and the suction cup.

Accordingly, it is a principal object of the invention to provide a feminine hygiene kit having a dedicated carrying case and personal hygiene articles.

It is another object of the invention to include within the kit articles for stanching the flow of bodily fluids.

It is a further object of the invention to enable disposal of soiled articles while overcoming leakage and objectionable odors.

Still another object of the invention is to enable suspension of the case from frequently encountered but generally unsuitable environmental surfaces.

It is again an object of the invention to secure hygiene articles resiliently to the case.

An additional object of the invention is to include within the kit a variety and plurality of absorbent hygiene articles.

Yet another object of the invention is to secure disposal bags and case attachment apparatus within the case.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
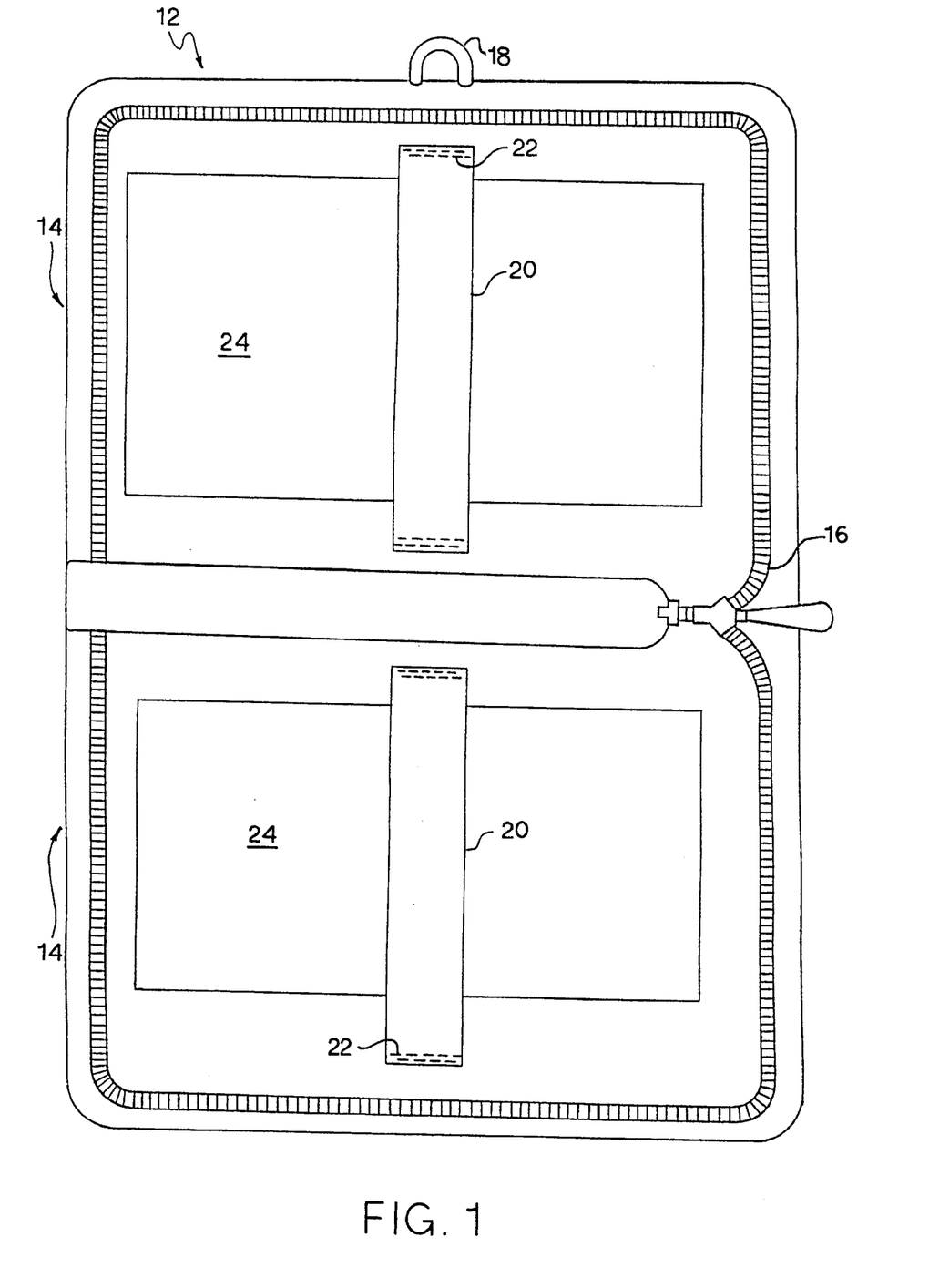
FIG. 1 is a plan view of the kit, with the carrying case fully opened to reveal internal construction and kit contents.

Turning now to FIG. 1 of the drawings, the novel feminine hygiene kit is contained within a case 12 having two corresponding sections 14 mating in clamshell fashion. A manually operable fastener, preferably a zipper 16, maintains case 12 closed. A loop 18 projects from case 12, for suspending case 12 in a manner to be described hereinafter.

A strap 20, which is preferably elastic for better retention of articles, although elasticity is not necessary, is attached to each section 14, as by stitching or by hook and loop material 22. Strap 20 is pulled away from the interior surface of section 14, and a feminine napkin 24 is placed thereunder. Strap 20 encircles and resiliently retains napkin 24 in place.

Figure 2:
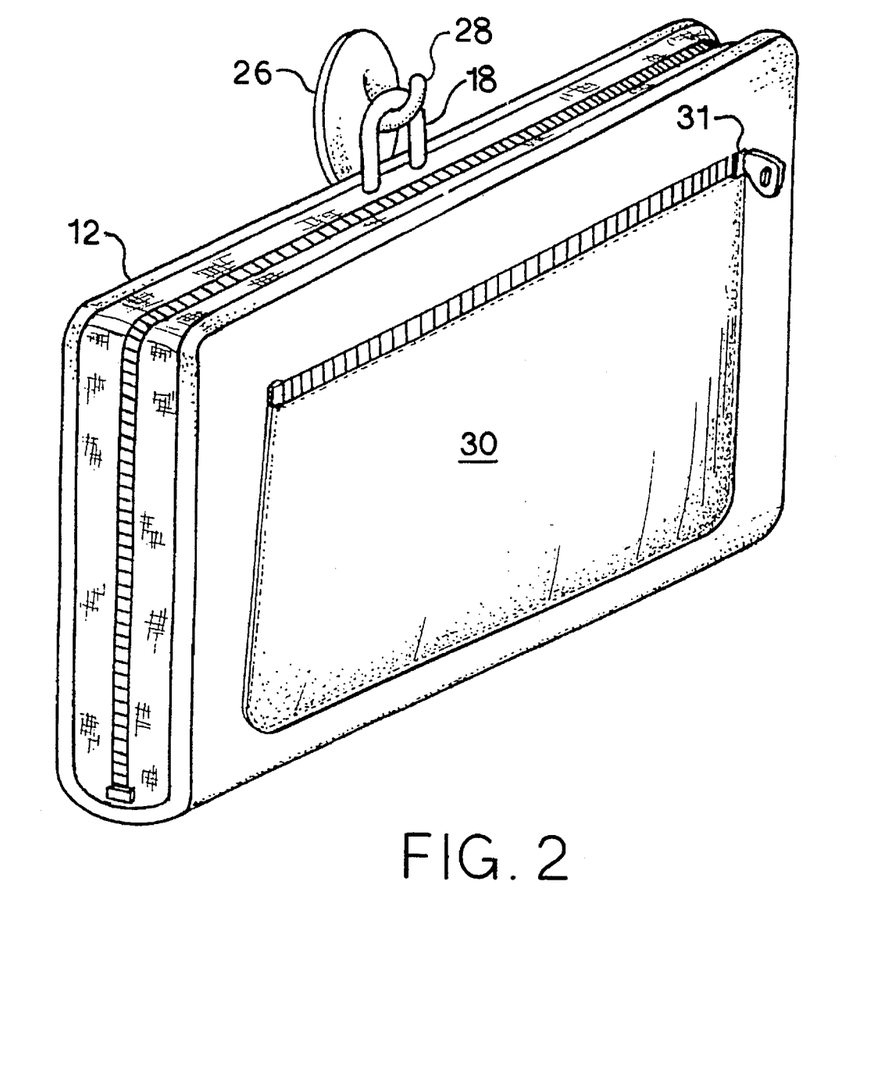
FIG. 2 is a perspective detail view of the kit, showing the case closed and suspended from a vertical surface.

As shown in FIG. 2, case 12 is of conventional construction, resembling a clutch or port-monnaie. Since it is possible that the necessity for employing the novel kit will arise when the user is in public, and has access only to a public washroom or like facilities, loop 18 is employed to suspend case 12 from a smooth vertical environmental surface (not shown), such as a wall of a commode stall. To accomplish this, attachment apparatus comprising suction cup 26 having an integral hook 28 is provided with the kit. Suction cup 26 adheres to the smooth environmental surface, and case 12 is suspended therefrom by engagement of loop 18 with hook 28. Suction cup 26 is stored in an external storage pocket 30 formed in case 12. Pocket 30 is closed by zipper 31.

Figure 3:
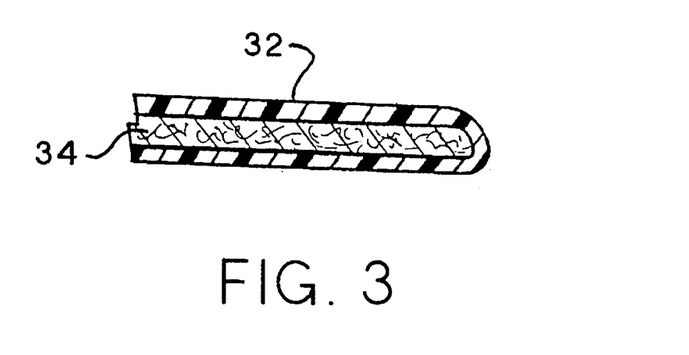
FIG. 3 is a cross sectional detail view showing construction of the sides of the case, drawn to enlarged scale.

As seen in FIG. 3, case 12 (shown in its entirety in FIG. 2) is washable, having a plastic or similar lining 32. In order to protect contents of the kit from deformation, the principal panel of sections 14 (see FIG. 1) are reinforced by a sheet of stiff material 34.

FIG. 1 shows a first embodiment of the invention, wherein two feminine napkins 24 are contained within the kit. Other products may be carried within the kit, and other arrangements are possible. Many absorbent, flexible products for stanching the flow of bodily fluids are available to the public, usually individually wrapped and sealed. These products vary in size and nature, and may include feminine napkins, tampons, panty shields, incontinence shields, and variations in size of the aforementioned articles.

While the principal application of the novel kit is to carry feminine hygiene articles of the types listed, it is not necessarily limited to this usage. For example, bandages, swabs, and other first aid articles may be included in the kit.

Nonetheless, it is most likely that users will be women who will select appropriate hygiene products, and carry the same within the kit. Other products and appropriate configurations for accommodating these products are shown in the further embodiments of FIGS. 4–6.

Figure 4:
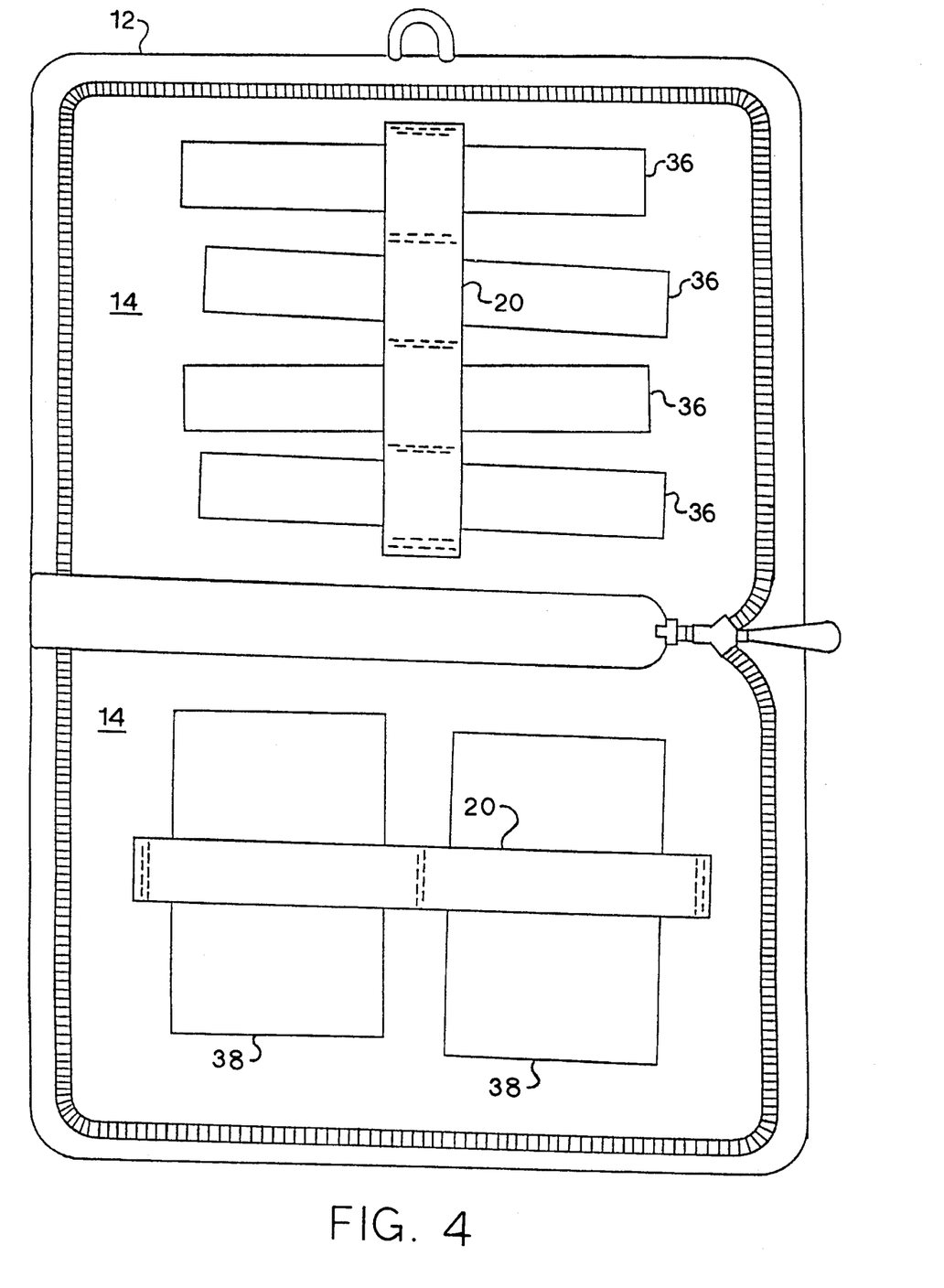
FIGS. 4, 5, and 6 are plan views equivalent to the view of FIG. 1, each showing an alternative interior arrangement of the case, and different kit contents.

FIG. 4 shows an embodiment wherein each strap 20 is stitched to its respective section 14 at several points, thereby enabling several articles to be secured by each individual strap 20. In the arrangement illustrated, four tampons 36 are retained at one section 14, and two panty liners or shields 38 are retained at the other section 14.

Figure 5:
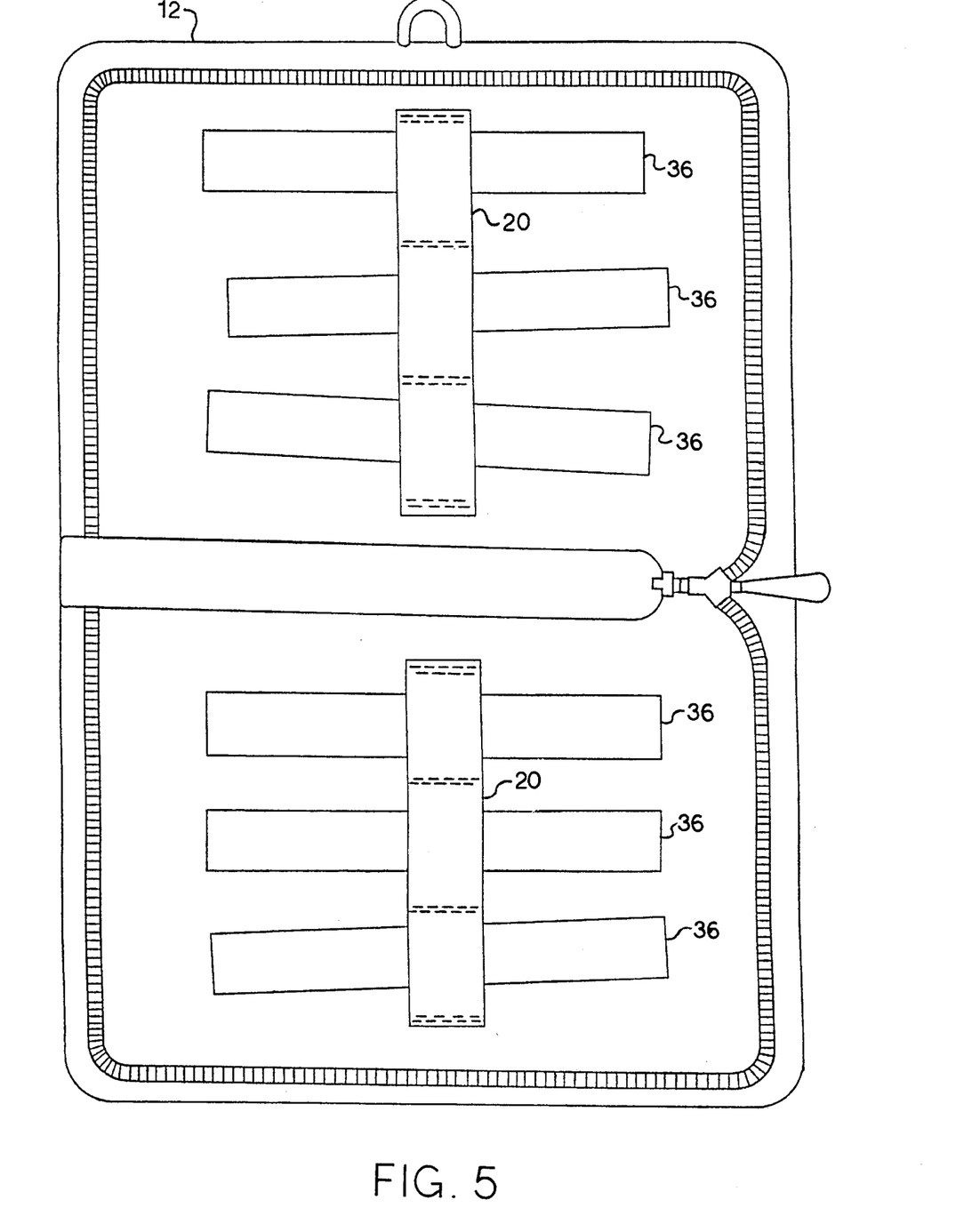

As shown in FIG. 5, straps 20 could be oriented similarly, and the novel kit could be arranged to store only tampons 36.

Figure 6:
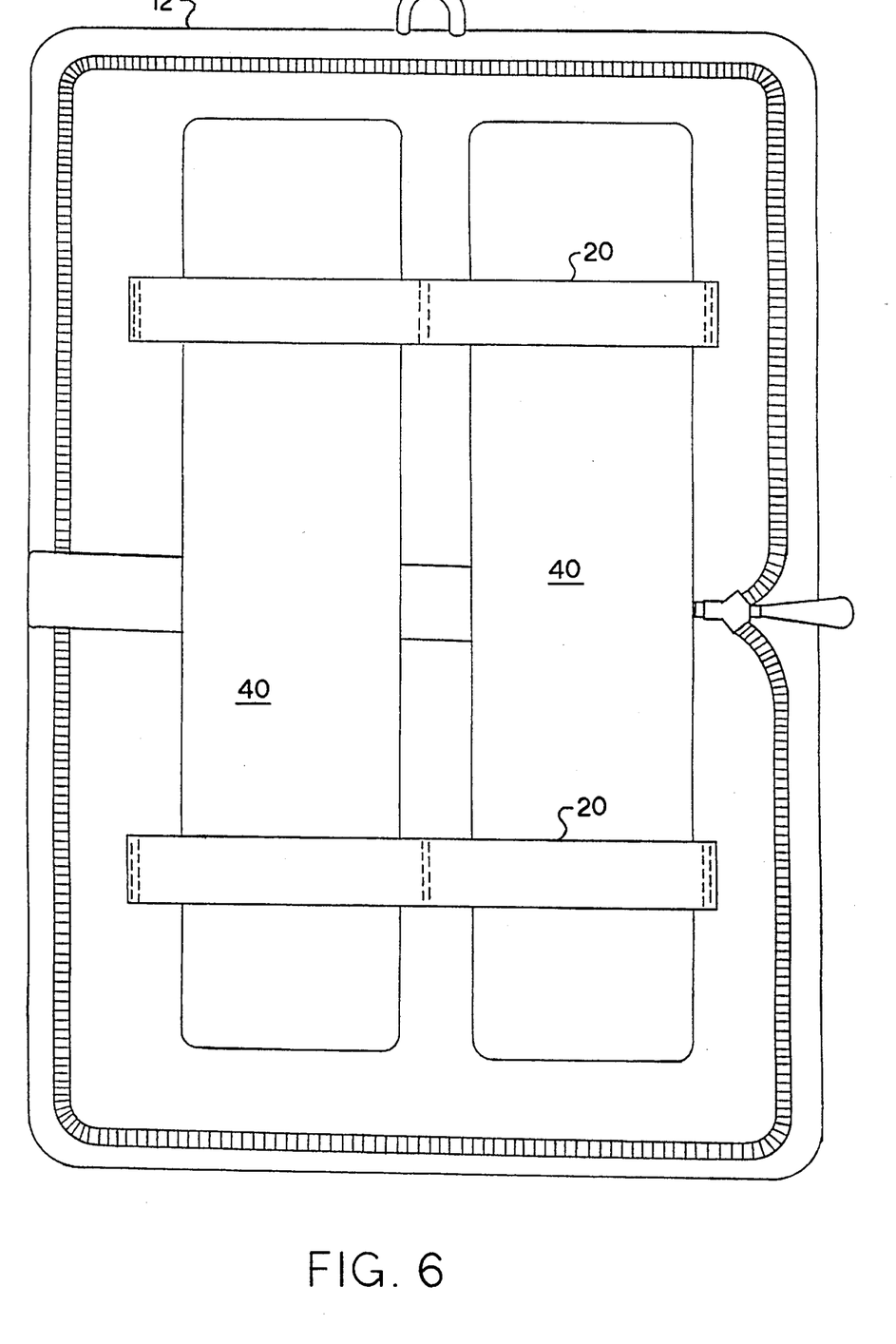
Figure 7:
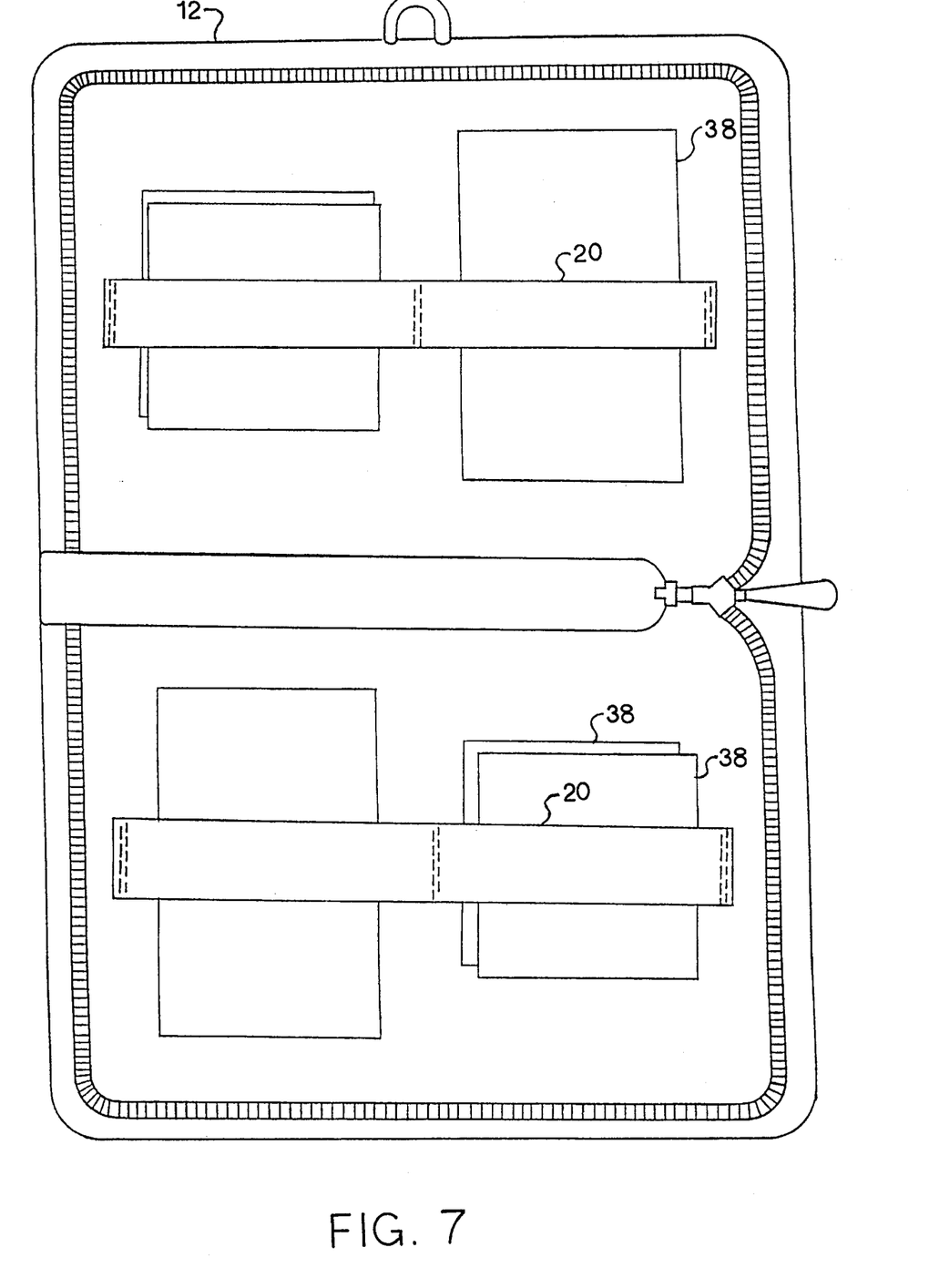
FIG. 7 is a plan view showing the case of FIG. 6, but illustrating different kit contents and storage arrangements.

In FIG. 6, straps 20 are arranged so that long feminine napkins 40 are accommodated by spanning both sections 14. Alternatively, as seen in FIG. 7, straps 20 arranged in the orientation illustrated in FIG. 6 may be employed to secure one or more shields 38.

Figure 8:
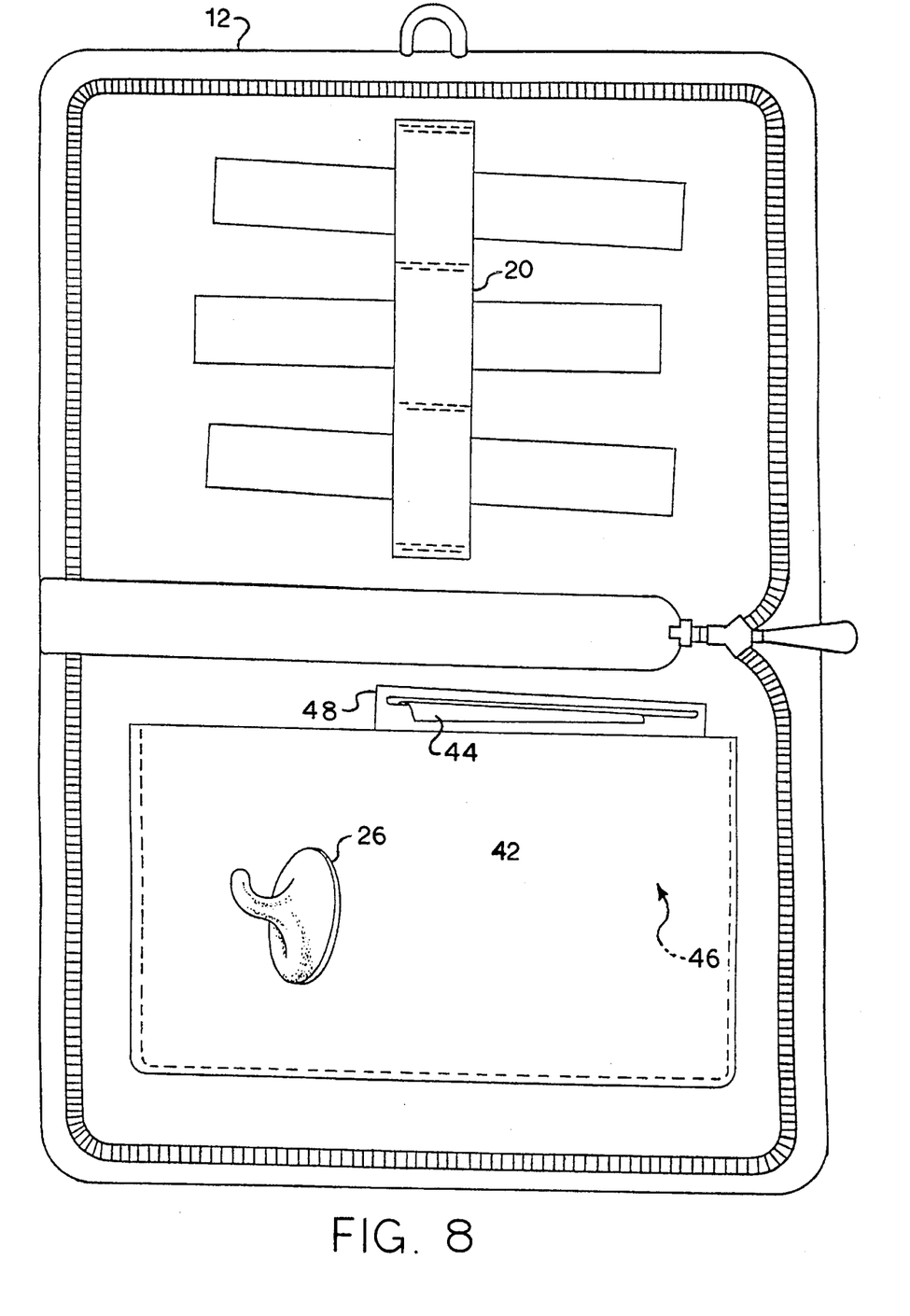
FIG. 8 is a plan view of another embodiment featuring an internal storage pocket formed in the case, and further illustrating a supporting suction cup and hook assembly in perspective, and disposal bags contained within the kit.

In a still further alternative embodiment, illustrated in FIG. 8, case 12 includes an interior storage pocket 42. Pocket 42 encloses suction cup 26, and also water impermeable bags 44 for enclosing soiled hygiene articles for subsequent disposal.

Since disposal may be necessary in a public place, it is desired to overcome objectionable odors which may accompany the soiled products. Bags 44 are of the sealable type, which may include interlocking tongue and groove members formed at the opening of the bag, or may include adhesive deposited upon the lips of the bag.

If tight sealing of a bag 44 cannot be assured, it is possible to further deodorize each bag 44, as by including a masking or deodorizing chemical or agent 46.

Bags 44 may be stored individually in pocket 42, in pocket 30 (see FIG. 2), or in a dedicated box 48.

It is to be understood that the present invention is not limited to the embodiments described above, but encompasses any and all embodiments within the scope of the following claims.

I claim:

1. A feminine hygiene kit comprising:

a case having two corresponding sections, each said corresponding section having a respective interior surface, said case including a manually operable fastener for selectively mating said corresponding sections in clamshell fashion, and a plurality of straps each fastened at both ends by hook and loop fastening material to the interior surface of at least one said corresponding section for retaining feminine hygiene objects within said case;

a loop fastened to an external surface of said case and a separate suction cup having a hook for attaching said case to an environmental surface by adhering said suction cup to the environmental surface and suspending said case from said suction cup by said loop;

at least one individually wrapped absorbent feminine hygiene object removably secured to said interior surface of said at least one said corresponding section by said straps; and at least one water impermeable bag removably contained within said case, for enclosing soiled products for disposal.

2. The feminine hygiene kit according to claim 1, further comprising a box for storing a said water impermeable bag.

3. The feminine hygiene kit according to claim 1, said water permeably bag having means for deodorizing said water impermeable bag.

4. The feminine hygiene kit according to claim 1, each said corresponding section interior surface having at least one said strap attached thereto.

5. The feminine hygiene kit according to claim 1, wherein said case further comprises an external storage pocket formed thereon.

6. The feminine hygiene kit according to claim 1, said straps being elastic straps.

7. The feminine hygiene kit according to claim 1 wherein at least one of said straps is fastened at an intermediate location between both said ends with hook and loop fastening material for retaining multiple feminine hygiene objects within said case.

* * * * *